(12) United States Patent
Sinnema et al.

(10) Patent No.: US 6,646,146 B1
(45) Date of Patent: Nov. 11, 2003

(54) NON-CORROSIVE CATALYTIC HYDROLYSIS OF FATTY ACID ESTERS TO FATTY ACIDS

(75) Inventors: Jacobus Sinnema, Antwerp (BE); Luc De Graef, Stekene (BE); Thomas Meisel, Brasschaat (BE); Inge Mussler, Kapellen (BE)

(73) Assignee: HaltermannAscot GmbH, Hamburg (DE)

( * ) Notice: Subject to any disclaimer, the term of this patent is extended or adjusted under 35 U.S.C. 154(b) by 31 days.

(21) Appl. No.: 10/048,998

(22) PCT Filed: Aug. 21, 2000

(86) PCT No.: PCT/BE00/00095

§ 371 (c)(1), (2), (4) Date: Apr. 8, 2002

(87) PCT Pub. No.: WO01/14304

PCT Pub. Date: Mar. 1, 2001

(30) Foreign Application Priority Data

Aug. 20, 1999 (EP) .............................................. 99202712

(51) Int. Cl.$^7$ ............................................. C07C 1/377
(52) U.S. Cl. ...................... 554/160; 554/156; 554/163
(58) Field of Search ................................. 554/156, 160, 554/163

(56) References Cited

U.S. PATENT DOCUMENTS 2,511,467 A    6/1950   Gresham ..................... 260/541

FOREIGN PATENT DOCUMENTS

| DE | 23213 | 7/1983 | |
|---|---|---|---|
| DE | 23464 | 8/1983 | |
| GB | 466596 | 5/1937 | |
| GB | 617929 | 2/1949 | |
| GB | 2 146 638 | 4/1985 | |
| GB | 2146638 | * 4/1985 | ........... C07C/27/20 |

* cited by examiner

*Primary Examiner*—Deborah D. Carr
(74) *Attorney, Agent, or Firm*—Jacobson Holman PLLC

(57) ABSTRACT

The present invention relates to a liquid phase process for the direct hydrolysis of a fatty acid ester to the corresponding fatty acid and alcohol in the presence of a catalyst, wherein the fatty acid in the liquid phase is contacted with steam in the presence of a compound of a metal that is capable of forming a soap with a large hydration shell as a catalyst.

10 Claims, 1 Drawing Sheet

NON-CORROSIVE CATALYTIC HYDROLYSIS OF FATTY ACID ESTERS TO FATTY ACIDS

Figure 1:
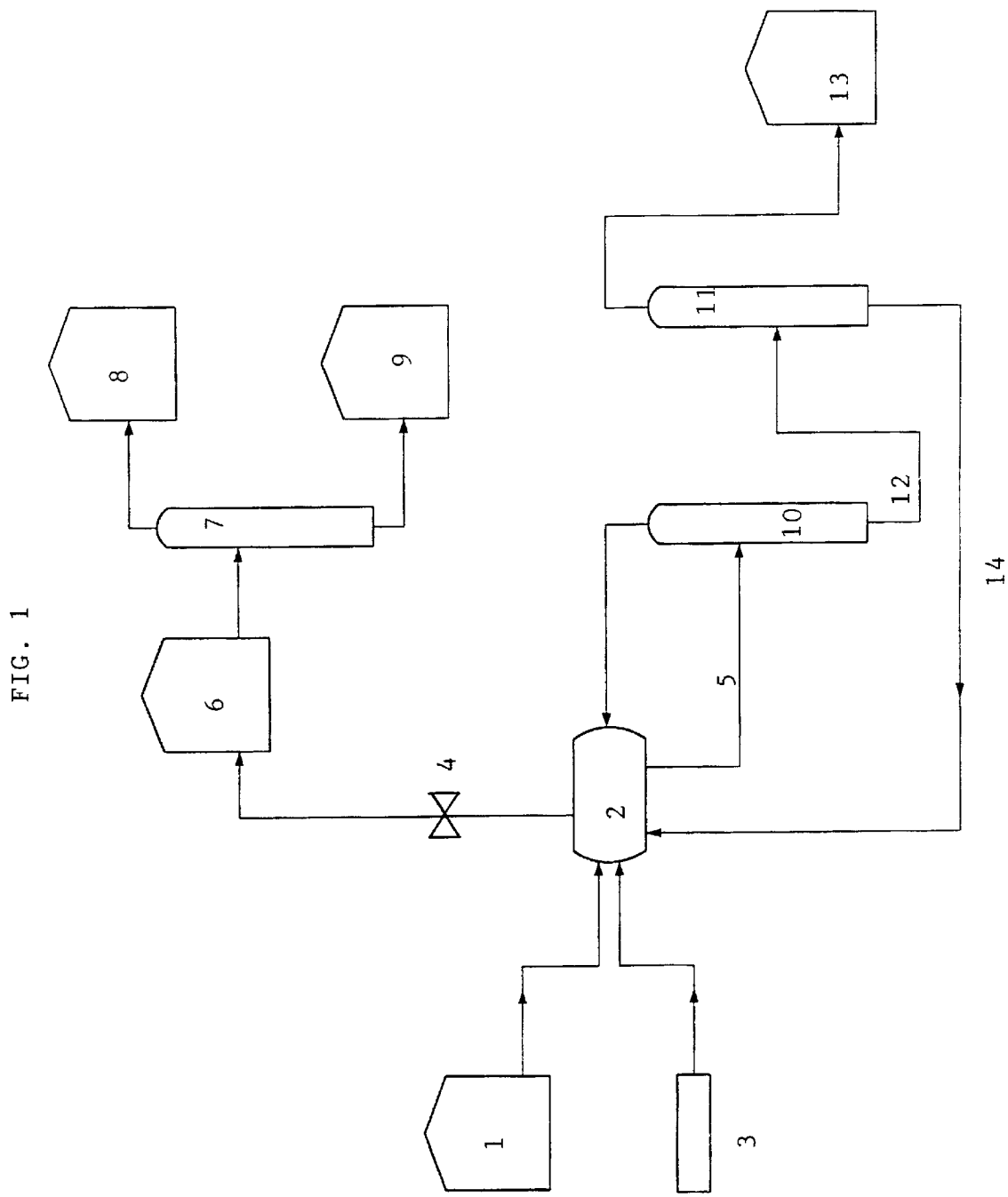

This application is a 371 of PCT/BE00/00095 filed Aug. 21, 2000.

This is a nationalization of PCT/BE00/00095 filed Aug. 21, 2000 and published in English.

The present invention relates to a process for a direct hydrolysis of a fatty acid ester to the corresponding fatty acid in the presence of a catalyst, as described in the preamble of the first claim.

Today fatty acids, in particular those fatty acids containing 6 to 20 carbon atoms, play a key role in modem technology and find numerous applications in lubricant formulations, food additives, plasticizers, etc. Thereby the fatty acids can either be used as single components or as a mixture of well-defined fatty acids. The main sources for the production of fatty acids are the native oils or tri-glycerides.

From GB-A-2.146.638 a process is known for the production of fatty acids starting from the corresponding lower fatty acid alcohol esters. In the process described in GB-A-2.146.638 the lower alcohol ester is hydrolysed in the presence of an acid catalyst, in particular a sulfonic acid and/or sulphuric acid catalyst. Water needed for the hydrolysis of the ester, is supplied to the system from the outside. Unreacted water and the lower alcohol formed upon hydrolysis of the ester are continuously distilled off. After completion of the hydrolysis reaction, the catalyst is separated from the crude fatty acid fraction by dissolution of the catalyst through water washing. Thereafter, the reaction mixture is often subjected to an additional treatment with a carbonate or hydroxide of an alkaline earth metal, to improve the quality of the mixture that is to be subjected to a distillation step, so as to recover the crude fatty acids therefrom.

The process disclosed in GB-A-2.146.638 however presents the disadvantage that the purity of the fatty acids recovered from the distillation step is insufficient. It appears that the fatty acid fraction recovered from the distillation contains impurities that originate from the catalyst.

There is thus a need to find an improved process for direct hydrolysis of fatty esters to the corresponding fatty acids, whereby the fatty acids can be obtained with an improved purity.

This is achieved in the present invention with the features described in the characterising part of the first claim.

In the method of this invention as a catalyst use is made of a compound of a metal capable of forming a.o. with fatty acids, preferably with the fatty acid to be recovered, a soap with a large hydration shell. Such compounds are well known to the man skilled in the art, and include compounds of Al, Ba, Ca, Cd, Co, Cr, Cu, Fe, Li, Mg, Mn, Ni, Pb, Sn, Sr, Ti, Zr, Zn. When adding such a compound or a mixture of two or more compounds to the reaction mixture, the compound is converted to form the catalyst therefrom, in situ. The catalyst is preferably added to the reaction mixture in the form of a compound which is a precursor for the catalyst, so that the catalyst is formed in the reaction mixture in situ.

With the process of the present invention fatty acids can be produced through direct hydrolysis of the corresponding fatty acid ester, in one single step, the amount of soap formed in the course of the reaction being limited.

The fatty acid can be recovered from the reaction mixture in a high purity of at least 99% and is virtually free of impurities originating from the fatty acid ester and the catalyst. The metal concentration appeared to be less than 1 ppm. Because of its high purity, the fatty acid obtainable with the method of this invention is suitable to be used as such in numerous applications where a high purity is an absolute prerequisite.

The fatty acid can be recovered from the reaction mixture by means of a two-pass distillation procedure. In a first distillation pass, unreacted fatty acid ester can be virtually completely distilled off from the reaction mixture. The bottoms of the first distillation pass containing the fatty acid and the catalyst, have been found to be virtually free of unreacted fatty acid ester, alcohol and water. These bottoms are subsequently submitted to a second distillation pass. The fatty acid recovered from the second distillation pass is obtained in high yield and high purity. It appeared namely that the catalyst is non-volatile and remains in the bottoms of the second distillation pass. In this respect it has also been found that, contrary to state of the art, the catalyst of this invention shows an excellent resistance towards decomposition and cracking when it is subjected to higher temperatures in the course of the distillation. As a consequence, the distillation to recover the fatty acid from the reaction mixture can be carried out while the catalyst and high temperature boilers are still present. This is time saving and allows to obtain a process with an improved efficiency. Moreover, the fatty acid recovered from the distillation has been found to be substantially free of cracking residues that may originate from the catalyst. The distillation bottoms containing the catalyst can be fed back to the hydrolysis step and be re-used several times without necessitating an intermediate regeneration or re-activation of the catalyst.

Also, contrary to the process known from the art, there is no need to subject the catalyst to any washing or pre-treatment to destroy the catalyst and allow the fatty acid to be recovered from the reaction mixture. In the process known from the state of the art namely, due to the corrosive nature of the catalyst, the catalyst must be carefully removed from the fatty acid containing fraction by water washing or distillation and the reaction as Well as the distillations must be performed in corrosion resistant materials, which is quite expensive.

The fact that the fatty acid can be recovered without necessitating to destroy the catalyst and the fact that the catalyst can be re-circulated to the reaction mixture as such without necessitating an intermediate regeneration or re-activation, are important economical advantages. In most catalytic processes often the catalyst is responsible for a large part of the costs.

From DE 23213 a process is known for the direct hydrolysis of fats of vegetal or animal origin to the corresponding fatty acids and glycerine by liquid water in the presence of a zinc compound as a catalyst. The process is carried out in an autoclave at a pressure of approximately 9 bar.

In GB-A-617.929 a process is disclosed wherein water and fat am subjected to countercurrent hydrolysis at high temperature, approximately 245° C., and high pressure in the presence of a water-insoluble metal soap catalyst. The molten fat is heated and pre-saturated with water by means of high pressure steam. Water is introduced in the reactor by means of a high pressure pump at a rate of about 45 wt. % of the rate of fat feed.

From U.S. Pat. No. 2,511,467 a vapour phase process for converting aliphatic alcohol esters of organic acids to their corresponding acids is known, wherein the ester is vaporised and passed over a catalyst with steam. As a catalyst use is made of a metal salt of an acid corresponding to the acid portion of the ester, for example zinc salts of the organic acids, supported on a suitable carrier material. The process is carried out at high temperature of 250–400° C. and a pressure of approximately 3 to 70 bar.

In GB 466 596 a process is disclosed for the continuous countercurrent hydrolysis of a fat to glycerine and the corresponding fatty acids by liquid water at high temperature (between 300° F. (149° C.) and 600° F. (316° C.)) and pressure, with or without the presence of a metal soap catalyst such as zinc soap, calcium soap and magnesium soap.

From DE 23 464a process is known for an emulsion hydrolysis of fats to glycerine and the corresponding fatty acids by liquid water at 165° C. and in the presence of $MgCO_3$, talc, chalk or thonerde as a catalyst.

In the process of this invention, preferably a catalyst is used which is an oxide, hydroxide, alkoxide or any other water soluble organic salt of the above mentioned metals. Preferably as a catalyst, an oxide, alkoxide or a salt of an organic acid of Zn, Sn, Al, Mg, Ti, Zr, Be, Ca is added to the reaction mixture. By making use of low molecular weight compounds, a relatively large amount of metal can be supplied to the reactor through a relatively small amount of catalyst. Very suitable catalysts are for example acetates or alkoxides of the metals mentioned above.

The compounds mentioned above have been found to show a good solubility in the present reaction mixture, and to be capable of easily forming the catalyst in the reaction mixture in situ. Also, these metals appear to show a high hydration shell when contacted with water, whereby the hydration shell may contain up to six molecules of water or even more. This is advantageous since the solubility of water in fatty acid ester has been found to decrease with increasing chain length of the ester. Typical water saturation concentrations of approximately only 0.1% by weight are found in a fatty acid ester with a chain length of 8 to 10 carbon atoms, which is rather low if an economically favourable reaction rate is aimed at. The hydrolysis of a fatty acid ester should in fact be regarded as a two-phase reaction, one phase containing the fatty acid ester, the other phase containing the water. In this reaction, the contact between the water and the fatty acid ester, and thus the hydrolysis of the fatty acid ester reactant by the water, is mainly restricted to the phase borderline. The catalysts of this invention have been found particularly capable of functioning as phase transfer catalysts. Due to the high degree of hydration of the catalyst, the water concentration in the fatty acid ester phase can be increased, thus allowing the reaction rate to be increased.

In order to accelerate the hydrolysis reaction, the alcohol reaction product is preferably continuously distilled off together with the excess of water. This is preferably performed by conducting steam through the reaction mixture, so as to allow the alcohol formed to be entrained by the steam. Water thus not only functions as a reactant, but also as a carrier for the alcohol formed in the course of the hydrolysis reaction. Also, with this steam stripping, most of the volatile impurities remaining in the reaction mixture, which cannot be removed by a pre-distillation of the fatty acid ester reactant, can be expelled together with the alcohol. Possible examples of such impurities include in particular low molecular weight impurities, for example phenol compounds. The fatty acid ester reactant is namely a natural product, which often contains impurities that may remain in the fatty acid after the hydrolysis and may adversely affect the colour and the odour of the fatty acid. In this way very pure fatty acids can be obtained, especially very pure C6–C10 fatty acids, with a low iodine value, good colour, a good stability towards oxidation because virtually all oxidisable products have been removed. This is particularly important when the fatty acids are to be used in cosmetic applications. The fatty acids obtainable with the present invention appear to show excellent heat stability, thus improving their storability.

The fatty acid ester used in the process of this invention is preferably a methyl ester of the fatty acid. The methanol formed upon hydrolysis of such an ester has a relatively low boiling point and can be easily entrained with the water.

The hydrolysis of the fatty acid ester of this invention is preferably carried out at an elevated, but moderate pressure, preferably between 3 and 20 bar so as to allow the water concentration in the organic ester phase to be increased. Below a pressure of 3 bar the water concentration in the organic ester phase is becoming low, thus involving a decreasing hydrolysis rate.

The process of the present invention presents the advantage that because of the heat stability of the catalyst, the reaction mixture can be distilled at a temperature, which is approximately the reaction temperature, by lowering the pressure to moderate under pressure, for example approximately 300 mbar. There is however no necessity to distil the reaction mixture at extremely low pressure so as to avoid on the one hand cracking or deactivation of the catalyst, and on the other hand contamination of the fatty acid end product by side products originating from undesired side reactions between fatty acid and/or fatty acid ester with the catalyst.

The water concentration in the organic ester phase can also be increased by carrying out the hydrolysis of the fatty acid ester at a temperature of between 150–250° C., preferably 180–230° C. Below 180° C. the reaction rate is getting low. Above 230° C. there is a risk that the fatty acid ester is cracked or is withdrawn from the reaction mixture together with the water.

The amount of metal added in the process of this invention is preferably varied between 0.01 to 0.2 percent by weight with respect to the weight of the ester, more preferably between 500 and 2000 ppm. At a concentration below 0.01 percent by weight hardly any catalytic effect can be observed. At a concentration above 0.2 percent by weight no further improvement or acceleration of the hydrolysis reaction could be found.

When producing well defined fatty acid cuts with a pre-determined number of carbon atoms, the fatty acid ester is preferably subjected to a preliminary distillation step, before being subjected to the hydrolysis reaction.

The process of the present invention can be either carried out as a continuous or a discontinuous process.

The process can be carried out as is shown in the preferred embodiment of FIG. 1.

In a possible procedure for carrying out the process of this invention, an amount of a fatty acid ester 1, preferably methyl ester, is supplied to a reactor 2 which contains a catalyst in an amount of 0.01–0.2 percent by weight of metal with respect to the weight of the ester 1. As a catalyst, preferably use is made of a compound containing one or more metals capable of forming with fatty acids a soap with a large hydration shell. Such compounds are well known from the art and include salts, organic salts, alkoxides, oxides, hydroxides and salts of organic acids of Al, Ba, Ca, Cd, Co, Cr, Cu, Fe, Li, Mg, Mn, Ni, Pb, Sn, Sr, Ti, Zr, Zn. Very suitable examples include ZnO, $Zn(CH_3COO)_2$, Zn-stearate. By using these virtually non-corrosive compounds as a catalyst, a virtually non-corrosive process can be obtained for the production of highly pure fatty acids, through direct hydrolysis of the fatty acid ester.

The reaction mixture is heated to a temperature of approximately 150–250° C. Steam 3 is supplied to the reactor 2. The pressure in the reactor 2 is maintained between approximately 3 and 22 bar. In the presence of water, the fatty acid ester is hydrolysed to the corresponding fatty acid and alcohol. The alcohol is expelled from the reactor 2 together with the excess of steam, through an over pressure valve 4 provided in the top of the reactor 2. If so desired, the alcohol/water mixture 6 can be separated in a distillation device 7, to give the alcohol 8 and water 9. The water 9 can be conducted as such to a wastewater treatment unit, without necessitating an additional purification.

The bottoms 5 of the reactor 2 which contain possible unreacted fatty acid ester, fatty acid, catalyst and high boilers, are directed towards a first distillation device 10. The unreacted fatty acid ester is distilled off and returned to the reactor 2. The bottoms 12 of the first distillation step 10 are virtually completely liquid and contain the fatty acid, the catalyst and high boilers. The bottoms 12 of the first distillation step 10 are preferably subjected to a second distillation step 11. Because the catalyst is non corrosive, there is no need to perform a water washing to separate the catalyst from the reaction mixture before a distillation can be carried out. As a consequence, the reaction mixture needs not be cooled before subjecting it to the distillation, which is in favour of the energy balance of the process.

The second distillation device 11 is kept at a temperature which is approximately the boiling temperature of the fatty acid, for example 220° C., to distil the fatty acid under normal conditions, but reduced pressure (e.g. approximately 300 mbar). The fatty acid 13 is recovered from the distillation in a high purity of 99% or more, and is suitable for direct use and needs no further refining or purification. The bottoms 14 of the second distillation step contain the catalyst in a virtually completely liquid state, and possibly also high boilers. The bottoms 14 are returned to the reactor 2.

The invention is further elucidated in the following examples.

EXAMPLE 1

Discontinuous Hydrolysis

To 1400 g of a C10-fatty acid methylester, 0.05% by weight with respect to the weight of the C10-fatty acid methylester of a $Zn(CH_3COO)_2$ catalyst was added. The mixture was heated in a pressure reactor to a temperature of approximately 220° C. and a pressure of approximately 4 bar. Water was supplied to the reactor at a supply rate of approximately 110 g/h, for approximately 9 hours. The pressure was kept constant by removing water, methanol and other azeotropic forming volatiles from the reaction mixture. After a reaction time of 9 hours the yield of crude fatty acid was 90%. The crude fatty acid was isolated from the reaction mixture by a distillation at 220° C. (200 torr), resulting in a pure fatty acid reaction product which excellent quality and low iodine value. The catalyst remained in the distillation bottoms and was further used as such in a subsequent hydrolysis, without subjecting it to a purification step.

EXAMPLE 2

Continuous Hydrolysis

To 1400 g of a C10-fatty acid methylester, 0.05% by weight of a dibutyltinoxide catalyst with respect to the weight of the C10-fatty acid methylester was added. The mixture was heated in a pressure reactor with a side stream take off, to a temperature of approximately 220° C. and a pressure of approximately 4–5 bar. The hydrolysis started off in a discontinuous manner at a temperature of approximately 220° C. As soon as approximately 65 wt. % of fatty acid (with respect to the total weight of the reaction mixture) was obtained, water and fatty acid methyl acid charged with 0.2 wt. % of catalyst, were supplied to the reactor through separate feed lines. Methanol was released via an over pressure valve in the top of the reactor together with the excess water and other volatiles. The crude reaction product contained 40–50 percent by weight of fatty acid and was collected as a side stream.

After the hydrolysis reaction had been terminated, the reaction mixture was distilled at 220° C. The first light fraction containing the methylester, was recycled to the reactor to be subjected to a repeated hydrolysis. The fatty acid was distilled off from the bottoms and obtained in high purity and quality. Per kg of water approximately 650 g of fatty acid were obtained.

What is claimed is:

1. A liquid phase process for the direct hydrolysis of a fatty acid ester to the corresponding fatty acid and alcohol in the presence of a catalyst, characterised in that the fatty acid ester in the liquid phase is contacted with steam. In that a compound of a metal capable of forming a soap with a large hydration shell is used as a catalyst and in that the reaction is carried out at a pressure between 43.5–290 psi.

2. A process as claimed in claim 1, characterised in that the metal is chosen from the group of Li, Zn, Sn, Al, Ba, Ca, Mg, Ti, and Zr.

3. A process as claimed in claim 1, characterised in that as a catalyst a compound is added which is an oxide, alkoxide, hydroxide or a salt of an organic acid of a metal capable of forming a soap with a large hydration shell.

4. A process as claimed in claim 1, characterised in that the alcohol is entrained from the reaction mixture.

5. A process as claimed in claim 1, characterised in that steam is conducted through the reaction mixture.

6. A process as claimed in claim 1, characterised in that the fatty acid ester is a methyl ester of the fatty acid.

7. A process as claimed in claim 1, characterised in that the fatty acid contains 6–20 carbon atoms.

8. A process as claimed in claim 1, characterised in that the hydrolysis is carried out at a temperature of between 150–250° C., preferably 180–230° C.

9. A process as claimed in claim 1, characterised in that the hydrolysis is carried out in the presence of 0.01 to 0.2percent by weight of metal with respect to the weight of the ester, preferably 500–2000 ppm of metal.

10. A process as claimed in claim 1, characterised in that the fatty acid ester is subjected to a pre-distillation step.

* * * * *